(12) United States Patent
Adel et al.

(10) Patent No.: US 7,684,039 B2
(45) Date of Patent: Mar. 23, 2010

(54) OVERLAY METROLOGY USING THE NEAR INFRA-RED SPECTRAL RANGE

(75) Inventors: Michael Adel, Zichron Ya'akov (IL); Aviv Frommer, D.N. Misgav (IL)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/557,880

(22) Filed: Nov. 8, 2006

(65) Prior Publication Data

US 2007/0187606 A1    Aug. 16, 2007

Related U.S. Application Data

(60) Provisional application No. 60/738,191, filed on Nov. 18, 2005.

(51) Int. Cl.
*G01B 11/00* (2006.01)
(52) U.S. Cl. .................................................. 356/401
(58) Field of Classification Search .................. None
See application file for complete search history.

(56) References Cited

U.S. PATENT DOCUMENTS

| | | | | |
|---|---|---|---|---|
| 2,571,307 | A | * | 10/1951 | Taylor ........................ 359/356 |
| 5,477,322 | A | * | 12/1995 | Webster ...................... 356/328 |
| 5,723,207 | A | * | 3/1998 | Lettington et al. .......... 428/216 |
| 5,835,214 | A | | 11/1998 | Cabib et al. |
| 5,856,871 | A | | 1/1999 | Cabib et al. |
| 6,142,629 | A | | 11/2000 | Adel et al. |
| 6,650,357 | B1 | * | 11/2003 | Richardson .................. 348/80 |
| 6,734,962 | B2 | * | 5/2004 | Treado et al. ............... 356/301 |
| 6,921,916 | B2 | | 7/2005 | Adel et al. |
| 7,132,201 | B2 | * | 11/2006 | Yin et al. ...................... 430/5 |
| 7,381,452 | B2 | * | 6/2008 | Goncalves Neto et al. .. 427/577 |
| 2001/0007498 | A1 | * | 7/2001 | Arai et al. .................... 356/401 |

(Continued)

FOREIGN PATENT DOCUMENTS

GB    2 357 158    6/2001

(Continued)

OTHER PUBLICATIONS

Frommer and Seligson, "Overlay mark performance: a simulation study", Proc. of SPIE vol. 5752 pp. 449-458 (2005).

(Continued)

*Primary Examiner*—Tarifur Chowdhury
*Assistant Examiner*—Gordon J Stock, Jr.
(74) *Attorney, Agent, or Firm*—Suiter Swantz pc llo (57) ABSTRACT

A method and tool for conducting NIR overlay metrology is disclosed. Such methods involve generating a filtered illumination beam including NIR radiation and directing that illumination beam onto an overlay target to produce an optical signal that is detected and used to generate overlay metrology measurements. The method is particularly suited to substrate applications having layers of opaque material that are transmissive in the NIR range (e.g., amorphous carbon) and where NIR imaging is used to obtain overlay measurements. A tool implementation includes a means for generating a filtered illumination beam extending into the NIR range and a detector for receiving NIR signal from an NIR illuminated target and a computer for processing the signal data to obtain overlay metrology measurements.

20 Claims, 7 Drawing Sheets

U.S. PATENT DOCUMENTS

2003/0002147 A1    1/2003    Chuang et al.
2004/0063008 A1*    4/2004    Tabery et al. ................. 430/30
2004/0233440 A1    11/2004    Mieher et al.
2004/0240064 A1*    12/2004    Dutta ......................... 359/573
2005/0012928 A1*    1/2005    Sezginer et al. ............ 356/401

FOREIGN PATENT DOCUMENTS

GB            2357158 A *    6/2001

OTHER PUBLICATIONS

U.S. Appl. No. 10/950,172, filed Sep. 23, 2004.
Written Opinion Mailed Jan. 7, 2008 from PCT/US06/44259.
International Search Report Mailed Jan. 7, 2008 from PCT/US06/44259.

* cited by examiner

OVERLAY METROLOGY USING THE NEAR INFRA-RED SPECTRAL RANGE

RELATED APPLICATIONS

The present application claims priority under 35 U.S.C. §119(e) from U.S. Provisional Patent Application No. 60/738,191 entitled "OVERLAY METROLOGY USING THE NEAR INFRA-RED SPECTRAL RANGE" filed Nov. 18, 2005, the entire disclosure of which is incorporated herein by reference for all purposes.

TECHNICAL FIELD

Inventive concepts described herein relate generally to methods and apparatus for projecting a near infrared (NIR) illumination beam onto a target substrate and detecting NIR optical signal from the target enabling accurate measurements of target properties. Particularly, the embodiments of invention refer to methods of conducting overlay alignment measurements of overlay targets formed with amorphous carbon layers formed thereon using NIR radiation to determine target alignment information. Additionally, the inventive embodiments concern measurements of surfaces and targets covered by amorphous carbon layers (a-CL) using NIR imaging.

BACKGROUND

Amorphous carbon is a material that is finding increasing usage in semiconductor processing. It is a particularly useful as a hardmask type material because of the nearly vertical sidewalls obtainable with this material. Additionally, high aspect ratios can be obtained using amorphous carbon layers. Additionally, amorphous carbon material is attractive because it can be formed into highly versatile etch stop layers. Accordingly, amorphous carbon layers (a-CL) have found wide acceptance and increasing utility in the semiconductor processing. Additionally, a-CL's find wide usage in many different layers of semiconductor manufacture. This includes the fabrication of overlay targets. Overlay targets are used for, among other things, determining the alignment of various layers of semiconductor substrates. These overlay targets are used in overlay metrology processes known to those having ordinary skill in the art. Overlay metrology is generally performed using bright field high magnification imaging or broadband spectroscopy or spectroscopic ellipsometry or scatterometry of metrology structures generated by semiconductor manufacturing patterning processes. Although suitable for their intended purposes, such approaches have certain limitations when used in conjunction with a-CL's. One of the difficulties is that imaging through a-CL's with visible light may lead to significant attenuation resulting in metrology performance degradation. In conducting overlay metrology using only visible light the presence of a-CL and other opaque (in the visible range) materials have caused a number of problems which the presently claimed inventive embodiments seek to remedy. The inventors have sought for and discovered new approaches for conducting metrology through amorphous carbon layers.

SUMMARY OF THE INVENTION

In accordance with the principles of the present invention, embodiments of the invention relate generally to improved methods of overlay metrology using near infrared radiation to enable the tools and methodologies which are discussed herein. Described aspects of the invention include, but are not limited to the embodiments detailed in the following description and drawings.

In one embodiment, the invention teaches a method for conducting near infrared measurements of a substrate having an amorphous carbon layer formed thereon. The process involves providing a substrate with an amorphous carbon layer formed thereon. An illumination beam is generated and filtered so that the filtered beam includes near infrared (NIR) radiation that is directed onto a sample surface to generate an optical signal. The optical signal is detected and processing to obtain metrology measurements of the substrate.

In a somewhat related embodiment the substrate includes an overlay target with the amorphous carbon layer. The filtered beam is directed onto the overlay target to generate an overlay signal that is detected and processed to calculate overlay measurements for the overlay target. Another somewhat related embodiment achieves the filtering after the substrate has been illuminated so that the surface generated optical signal is filtered.

In an apparatus embodiment, a near infrared overlay metrology system comprises the following elements. A movable stage for holding a substrate with an overlay target formed on the substrate. An illumination source for generating an illumination beam that includes near infrared (NIR) radiation. A filter element that filters the illumination beam to enable the passing of visible and near infrared (NIR) radiation. Beam directing optics arranged to direct the beam through an objective optical system to focus the illumination beam on the overlay target to generate an overlay signal. A focusing optical system that receives the overlay signal and directs the overlay signal onto a detector system and processing electronics for processing the overlay signal and calculating overlay measurements for the overlay target.

In another apparatus embodiment, a near infrared overlay metrology system comprises an illumination source for generating an illumination beam including near infrared (NIR) radiation. A filter element for receiving the illumination beam and filtering the illumination beam to include NIR radiation. An optical system arranged to direct the beam onto an overlay target formed on a substrate to generate an overlay signal. A detector system arranged to receive the overlay signal and processing electronics for processing the detected overlay signal and calculating overlay measurements for the overlay target. What is the difference between 0006 and 0007?

These and other aspects of the present invention are described in greater detail in the detailed description of the drawings set forth hereinbelow.

BRIEF DESCRIPTION OF THE DRAWINGS

The following detailed description will be more readily understood in conjunction with the accompanying drawings, in which.

It is to be understood that, in the drawings, like reference numerals designate like structural elements. Also, it is understood that the depictions in the Figures are not necessarily to scale.

DISCLOSURE

In general, embodiments of the present invention provide mechanisms for conducting measurements through amorphous carbon layers (a-CL). With particular embodiments performing overlay metrology by either imaging or spectroscopy in the near infra-red (NIR) spectral range. The infra-red range is defined as a wavelength range that is substantially outside the visible range of wavelengths and typically includes longer wavelengths than about 650 nm. The NIR comprises wavelengths from about 650 to 1200 nm, or more specifically from 700 to 1000 nm. The inventors have discovered certain advantages that accrue with certain bandwidths in the NIR range. Certain particular embodiments are useful in the 750 to 1100 nm range, the 800 to 1100 nm range and also the 850 to 1100 nm range or any sub-band in these ranges. Also, the embodiments of the present invention envision extended spectral range metrology analyzing signal extending from the visible range all the way into the NIR range.

The inventors have discovered that the NIR spectral band has specific advantages when applied to certain layers which are substantially opaque in the visible wavelengths. In one particular example, an amorphous carbon layer (a-CL) may be considered.

Figure 1A:
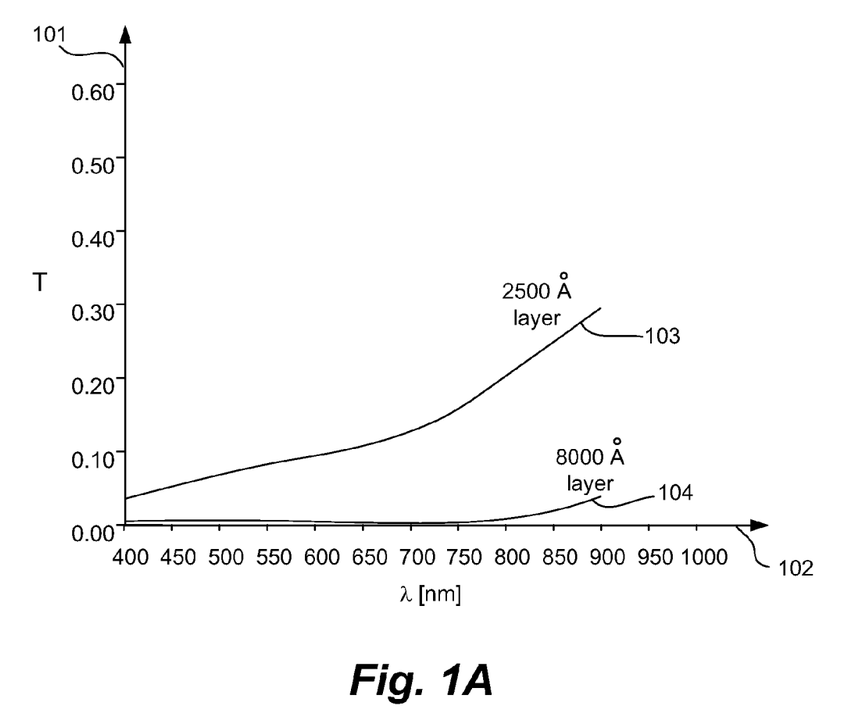
FIG. 1A is a graphical depiction of the transmission behavior of amorphous carbon layers (a-CL's) over a range of wavelengths extending into the near infrared (NIR) range.

FIG. 1A is a depiction of transmission (T) (axis 101) as a function of wavelength (in nanometers along axis 102) of a 2500 Å (Ångstrom) thick a-CL layer 103 and a 8000 Å thick a-CL layer 104. It is easily seen that the transmission signal increases dramatically as the illumination signal passes from the visible range into the NIR range. FIG. 1A shows that as the a-CL layer thickness increases the transmission is reduced and pushed to higher wavelengths. Other semiconductor materials, such as ZnSe and Si, can be shown to exhibit similar behavior. In addition to having high transmission through substantially thicker layers of opaque material, the amount of light available in an illumination beam can be substantially increased due to the abundance of NIR emissions produced by many light sources (e.g., tungsten halogen sources).

In one specific embodiment, only light in the NIR is used, avoiding complications in the metrology due to so called chromatic aberrations in the metrology system. In particular, for some wafers, one part of the overlay target reflects more in the visible while the other reflects primarily in the NIR. In this case by eliminating the visible entirely the detrimental effects of chromatic aberrations can be significantly reduced.

In another embodiment, use is being made of another advantage of extending the spectral range into the NIR. Even in the cases where the structures under the opaque layers can be observed when using only the visible spectral range, the image would be formed by a very narrow spectral band—only the long wavelengths that can penetrate through the opaque layer. However, it was shown that in the presence of process variations, overlay metrology by a narrow spectral band results is degraded precision and TIS variability.

Figure 1B:
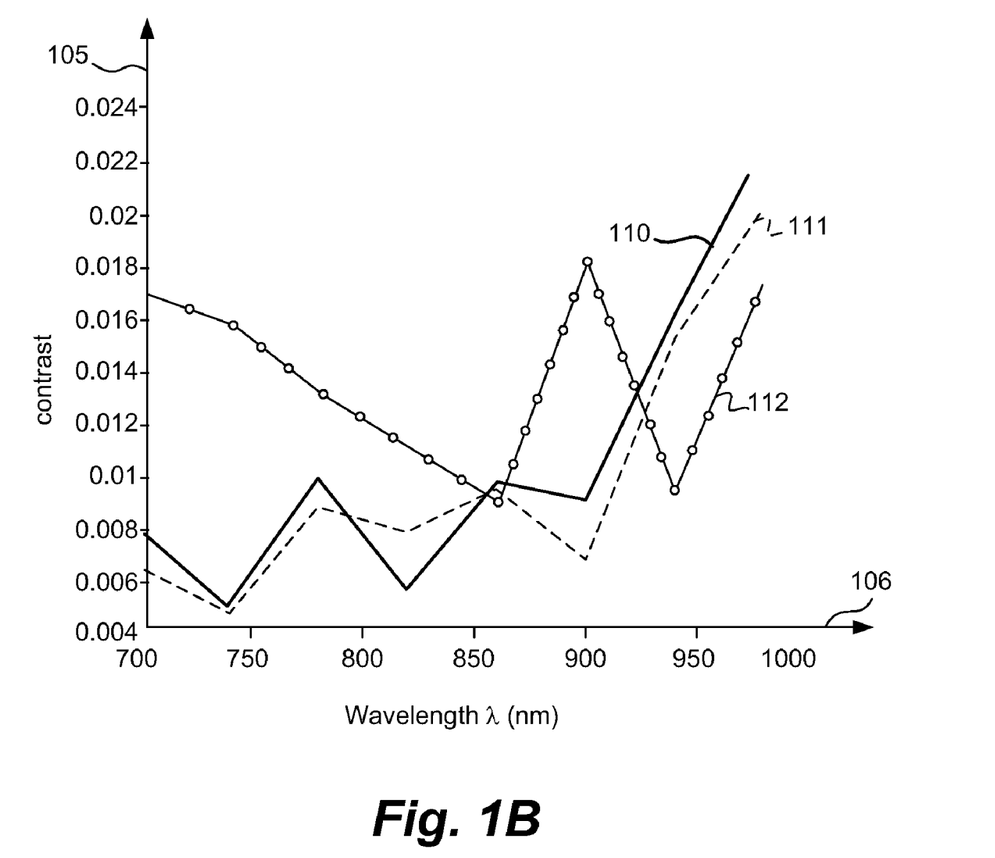
FIGS. 1B & 1C are graphical depictions of the contrast behavior and tool induced shift (TIS) behavior of a-CL's of varying thicknesses over a range of wavelengths in the near infrared (NIR) range.
Figure 1C:
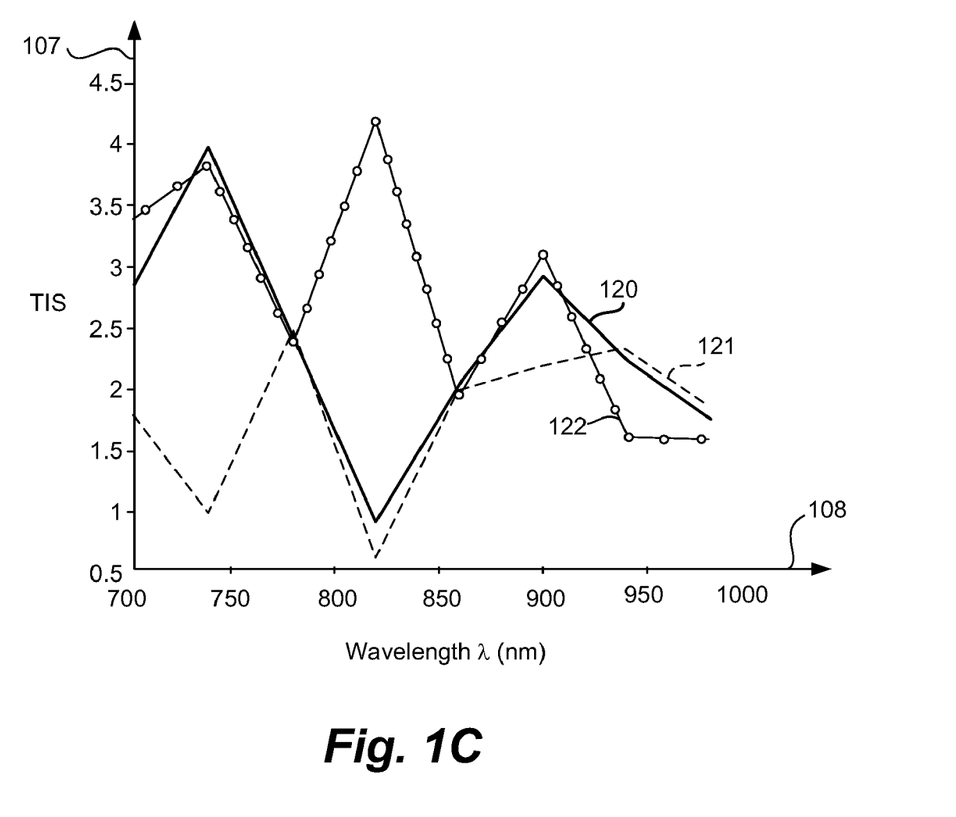

Additionally, due to the wide range of process variants and materials that comprise amorphous carbon materials signal spectra can vary substantially. FIGS. 1B and 1C depict process variation results that show a spectral shift of the signal spectra between the process variants. FIGS. 1B and 1C show results from three different process variants in a process layer including an a-CL. FIG. 1B describes signal contrast as a function of a-CL thickness and wavelength. FIG. 1C describes tool induced shift (TIS) as a function of a-CL thickness and wavelength. The structure simulated is a 2 um wide trench in Si filled with $SiO_2$, and covered with a hard-mask layer stack containing a-CL. This structure has been simulated for three different process variants: (i) Nominal a-CL thickness (e.g., about 300 nm thick)(depicted as unbroken lines 110, 120), (ii) An a-CL thicker by 5% than nominal (depicted as dotted unbroken lines 112, 122), (iii) An a-CL thinner by 5% than nominal (depicted as dashed lines 111, 121).

The change in the reflectance of the overlay target as a function of wavelength changes the spectral behavior of the signal contrast and TIS (tool induced shift) across the wafer. As a result different overlay metrology performance is observed at different wafer locations. The signal contrast is defined, using the maximum and minimum values of the signals, as:

$$\text{Contrast} = \frac{I_{max} - I_{min}}{I_{max} + I_{min}} \qquad \text{Equation 1}$$

FIG. 1B shows the contrast for the three process variants simulated. Contrast (axis 105) is plotted against the cut-off wavelength of the illumination band (wavelength in nm on axis 106). Illumination was simulated to pick up at 450 nm. However, since the a-CL does not transmit enough light in the short wavelength range to be easily detectable, the wafer reflectance practically begins at ~650 nm. The trend shown is that as the practical spectral range is broadened the smaller is the contrast variation across the wafer. In cases where a strong change in contrast occurs at the working spectral band, this will result in a drop in measurement precision in those wafer locations where contrast is low, and in an overall poorer precision of the overlay measurement.

FIG. 1C depicts the effect on TIS for the three process variants simulated. TIS is caused by asymmetrical optical aberrations, $3^{rd}$ order coma being the most dominant one. An important aspect of the asymmetric aberrations in terms of overlay metrology is their different interaction with different process layers. Depending on the shape of the signal from the particular layer, a given amount of aberration will shift the image at a different magnitude. It is well known that obtaining low TIS on one process layer does not guarantee low TIS on another process layer. A set of asymmetric aberrations can be assumed to be constant across the field of view (FOV) and constant across all wavelengths, and the TIS resulting from the different interaction of the signals with these asymmetric aberrations has been simulated. TIS variability is calculated as a result of the different TIS-values between the three simulated process variants. FIG. 1C shows TIS (axis 107) plotted against the cut-off wavelength (axis 108) of the illumination band. The trend shown is that as the practical spectral range is broadened the smaller is the TIS variability across the wafer.

As shown in FIGS. 1B and 1C, the addition of NIR to the inspection spectrum will expand the effective spectral range used for the optical metrology and will result in superior performance of the metrology in the presence of process variations. Further details of such inspection approaches are detailed in a paper entitled: "Overlay mark performance: a simulation study", by Aviv Frommer and Joel L. Seligson, published in Proc. of SPIE Vol. 5752 pp. 449-458 (2005) which is hereby incorporated by reference.

Extending the metrology spectral range generally involves using a light source emitting light at the desired spectral range, allowing the light to go through the system and designing the rest of the optical system to transmit light and perform optically adequately in this spectral range. For example, the coating utilized for the optical components would need to be selected to withstand NIR light passing through them. A heat management system as described further below may also be utilized in conjunction with design of the optical components.

In general, any suitable optical metrology tool may be modified to incorporate one or more filters extend the wavelengths into the desired range and these filter(s) are inserted in the illumination. Although embodiments of the present invention are mainly described in reference to a tool for measuring overlay, other types of metrology tools may be utilized, such as a CD metrology tool. Additionally, any suitable metrology techniques, such as overlay and CD determination techniques, may be utilized. Several modifiable overlay systems and overlay determination techniques are further described in (1) U.S. Pat. No. 6,921,916, entitled OVERLAY MARKS, METHODS OF OVERLAY MARK DESIGN AND METHODS OF OVERLAY MEASUREMENTS, issued 26 Jul. 2005,by Michael Adel et al., (2) U.S. patent application No. 10/785,396, entitled APPARATUS AND METHODS FOR DETECTING OVERLAY ERRORS USING SCATTEROMETRY, filed 23 Feb. 2004 by Walter D. Mieher et al., and (3) U.S. Pat. No. 10/950,172, entitled APPARATUS AND METHODS FOR DETERMINING OVERLAY AND USES OF SAME, filed 23 Sep. 2004 by Mark Ghinovker et al., which patent and applications are hereby incorporated by reference in their entirety.

Figure 1D:
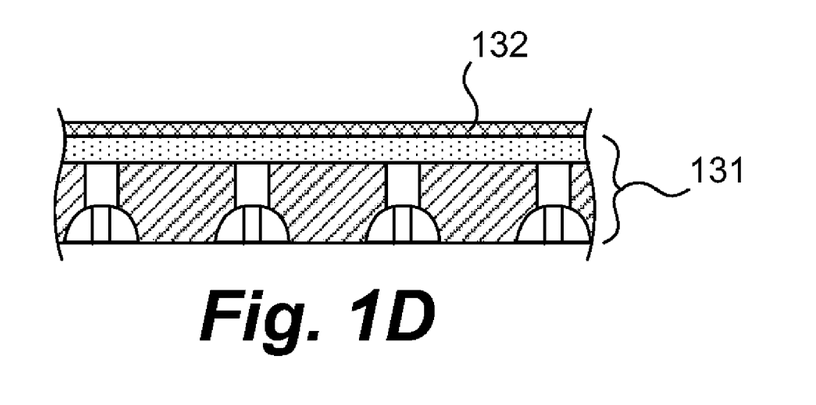
FIGS. 1D, 1E, & 1F are simplified schematic depictions example applications of a-CL's in various substrate implementations including overlay targets.
Figure 1E:
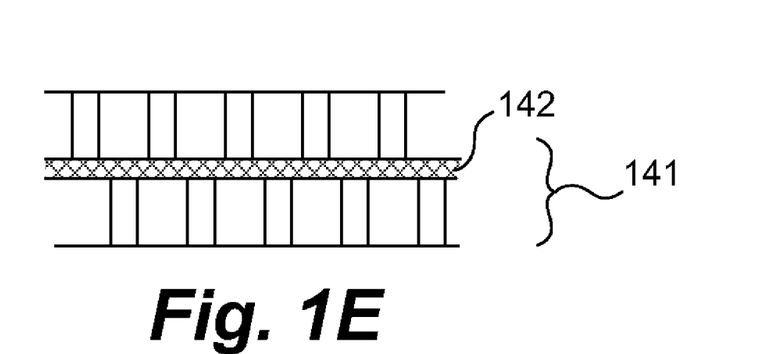
Figure 1F:
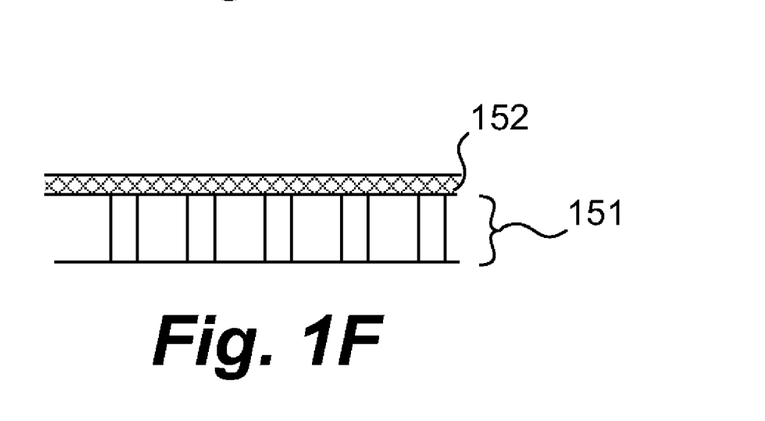

FIGS. 1D, 1E, & 1F provide a few simplified examples of substrate surfaces having a-CL's that would benefit from NIR illumination and metrology. FIG. 1D provides a simplified illustration of a substrate having a multiplicity of transistors formed (layer 131) on the substrate and having an a-CL 132 formed thereon. FIG. 1E provides a simplified illustration of a substrate having one embodiment of overlay target 141 having an a-CL 142 formed thereon. FIG. 1F provides a simplified illustration of a substrate having another embodiment of overlay target 151 having an a-CL 152 formed thereon. These embodiments and many other can benefit from NIR metrology as discussed herein.

In certain embodiments described herein, a hot mirror can be used to extend the wavelength range of an illumination beam to cover long wavelengths, for example, having a range between 650 to 1200 nm, or more specifically from 700 to 1000 nm. In conventional systems, a hot mirror is actually used to cutoff wavelengths in the NIR range or above. In one embodiment, a hot mirror may also be used, but to cutoff wavelengths that extend well into the NIR or beyond, e.g., above 1000 or 1200. The range depends on the particular materials utilized and the configuration of the system, e.g., its ability to handle heat generated by the NIR. In other implementations, a NIR band pass configuration may be used filter an illumination beam so that only the NIR range of wavelengths are creating a selective NIR beam. In this latter embodiment, a visible band pass or low pass filter may be also used and selectively switched with the NIR band pass filter to selectively pass visible and NIR for differently transmissive materials. For instance, the NIR band pass filter may be used for materials that transmit well in the NIR range, while a visible range pass filter may be used for materials that transmit well in the visible range. Any suitable NIR low pass or band pass filter may be utilized. For example, NIR low pass and band pass filters (as well as visible band pass filters) are available from Andover Corp. of Salem, N.H.

Figure 2:
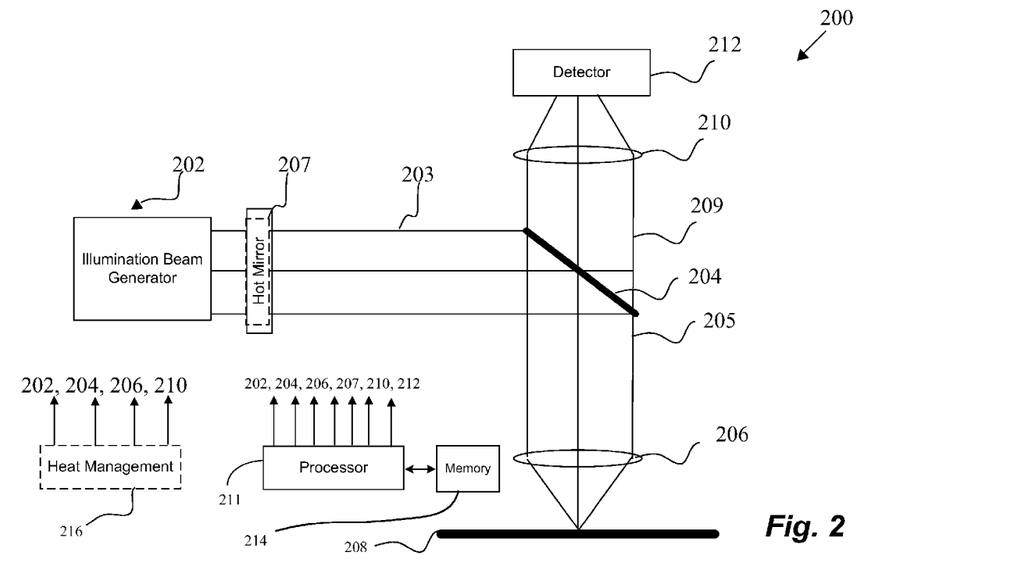
FIG. 2 is a schematic depiction of a near infrared metrology system of a type suitable for obtaining metrology measurements in accord with the principles of the invention.

FIG. 2 is a simplified diagrammatic representation of a general metrology system 200 in accordance with one embodiment of the present invention. The depicted system 200 is capable of overlay metrology applications. As shown, the system 200 includes a beam generator 202 for producing an incident beam 203 of electromagnetic radiation. A tungsten halogen source is suitable for producing the desired illumination beam. Other halogen sources (e.g., Xenon sources and the like), lasers, LED's, and other sources capable of producing substantial NIR radiation are also suitable. The incident beam 203 is directed into a filter system and then into a beam splitter 204 for directing the incident beam 205 towards the sample 208. Typically, the incident beam 205 is focused onto the sample by an objective optical system 206. An output beam 209 is then obtained from the sample in response to the incident beam 205 and passed through the beam splitter 204 through relay optical lens system 210 and onto detector 212. The detector 212 generates an image or output signal of the sample based on the output beam 209. In one implementation, the detector 212 includes an imaging array (CCD arrays and the like) capable of capturing image data from the sample.

The system 200 also includes a processor 211 and one or more memory elements 214 which are configured to control the various components, such as the beam generator 202, objective lens 206, and detector 212 and so on. The processor 211 and memory 214 can be configured to analyze the detected output beam. In particular, in an overlay application the processor 211 and memory 214 analyze a detected image or output beam and implement any of a number of various overlay determination techniques known to those having ordinary skill in the art. Typical examples of such techniques are described in the various overlay determination techniques described in the above referenced applications.

In this system 200 a filter 207 is placed in the illumination path after the source 202. In one implementation, the filter comprises a hot mirror 207 configured to selectively filter the beam 203. The placement of the hot mirror 207 with respect to the components in the illumination path is merely exemplary and is not meant to limit the scope of the invention. To clarify, the hot mirror may be placed anywhere along the illumination path so as to filter the illumination and extend the wavelengths into the desired NIR range. The inventors point out that many such filters known to those having ordinary skill in the art may be employed. Such include, but are not limited to, multi-layer reflective and absorption filters. The applicants specifically contemplate that any set of filters can be employed to accommodate the desired wavelengths for the illumination beams. In particular, low pass filters configured to filter the illumination beam so that it includes NIR and visible radiation, but not longer wavelengths (i.e., those above 1.1 µm). In particular, filters configured to pass a wide bandwidth of radiation extending into the NIR range are contemplated. Examples include filters enabling wavelengths from about 40 nm to about 70 nm to pass, or even extending from about 40 nm to 80 nm. However, the inventors point out that the invention is not limited to such. Other bandpass filters optimized to enable a narrow bandwidth of radiation in the NIR range are also contemplated. Particular examples of such filters include 0.75 µm-1.1 µm bandpass filters, 0.80 µm-1.1

μm bandpass filters, 0.85 μm-1.1 μm bandpass filters and other such filters perhaps extending only to about 1.0 μm. As shown in FIG. 1A these ranges offer particularly good performance when used for metrology through a-CL. It should be noted that additional narrow bandpass filters for any subband of the above mentioned bands may also be incorporated.

The inventors point out that one of the serious drawbacks to such NIR metrology in the past has been the limitations (and expense) inherent in attempting to obtain measurements over such a broad bandwidth illumination wavelengths. In particular, when an inspection or metrology microscopy system uses a broad bandwidth of light to illuminate a subject, the problems of chromatic aberration become very difficult to remedy in a cost effective manner. The inventors have addressed this problem by employing optical systems (206, 210) having very low orders of chromatic aberration across a relatively broad spectrum of light. Such chromatically corrected optics demonstrate longitudinal chromatic correction of at least 100 nm over the entire operational bandwidth (e.g., in one case over the visible and NIR regime) and also demonstrate lateral chromatic correction of at least 50 nm over the entire operational bandwidth. Of course over a bandpass system in the NIR regime this is easier and less expensive to achieve. One example of an implementation that can be employed to obtained sufficient chromatic aberration correction is taught in the patent application entitled: "High NA System for Multiple Mode Imaging" invented by Chuang et al. having a U.S. Pat. Publ. No. 20030002147 and filed on 2 Jan. 2003 which is hereby incorporated by reference for all purposes.

A heat management system 216 may also be utilized to handle heat caused by the NIR range of light. For example, one or more heat sinks may be used at the holders of the one or more optical components to draw heat off such components. Other types of mechanisms for drawings heat or cooling the optical components may also be utilized.

Figure 3:
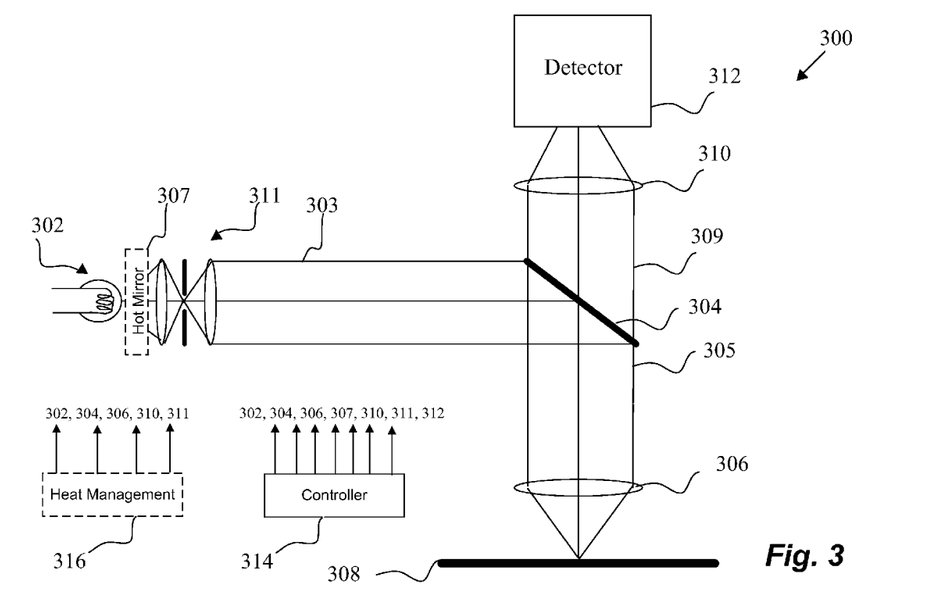
FIG. 3 is a schematic depiction of another embodiment of a near infrared metrology system of a type suitable for obtaining metrology measurements in accord with the principles of the invention.

FIG. 3 illustrates an embodiment of a microscopic imaging system 300 in accordance with one embodiment of the present invention. This system 300 can have components which operate like the components of FIG. 2. In this example, an illumination source 302 is directed through a hot mirror filter element 307 which is configured to be interchangeable with a number of other filter elements 307 that can be selected for desired illumination beam properties. The illumination beam passes through illumination optics 311 which include focus and correction optics and a ring aperture (enabling telecentricity). The incident beam 303 is directed by beamsplitter 304 onto the sample 308 where a output beam (output optical signal) is generated. The output signal 305 is collected by optical system 306 and directed through the beamsplitter 304 onto optic (e.g., tube lens) 310 as image signal 309 and onto detector 312. In this depiction, the detector is in the form of a camera 312 for producing an image of the sample 308. As shown, and explained above, the hot mirror 307 may be placed at any point along the illumination path. As before, the heat management system 316 may also be utilized as described above. Also as discussed above, a control system 314 may also be utilized to control a variety of systems (including, but not limited to, 302, 304, 306, 307, 310, 311, 312) as described above.

Figure 4:
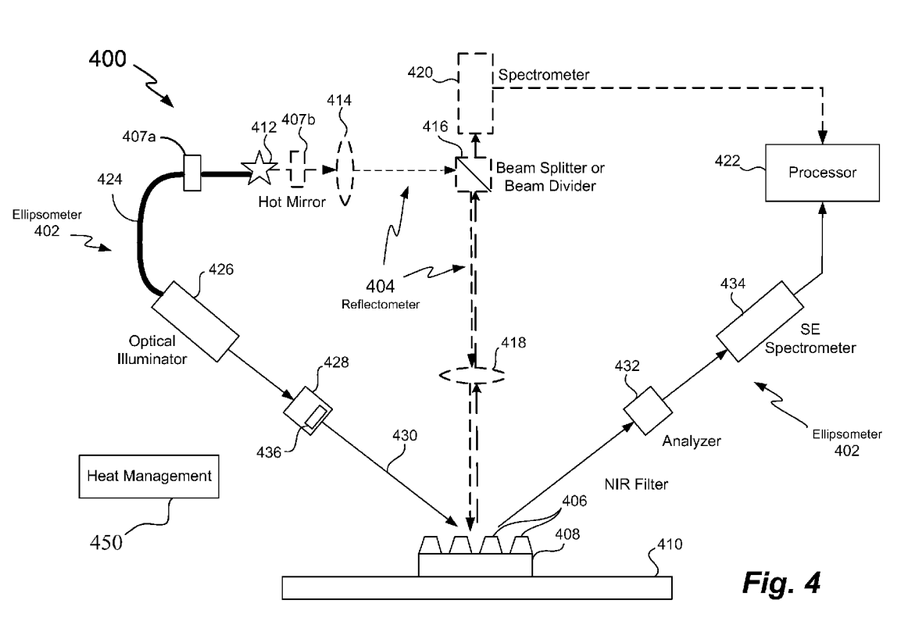
FIG. 4 is another schematic depiction of yet another embodiment of a near infrared metrology system suitable for obtaining metrology measurements in accordance with the principles of the invention.

FIG. 4 is a simplified schematic view of an embodiment of a spectroscopic scatterometer system 400, in accordance with one embodiment of the present invention. This system 400 combines the features of a spectroscopic ellipsometry system 402 and spectroscopic reflectometery system 404 (depicted generally with dashed lines), each of which may be used for measuring overlay of a grating structure 406 disposed on a substrate or wafer 408. Of course, a system that has only a spectroscopic ellipsometer 402 or only a spectroscopic reflectometer 404 may also be utilized.

One example of an overlay type target is a grating structure 406, for example, as described in the above referenced Walter D. Mieher et al. application. The grating structure 406 (depicted here in a simplified illustration) can be widely varied. The grating structure 406 may, for example, correspond to any of those grating structures described herein as well as many others known to those having ordinary skill in the art. Both the spectroscopic ellipsometer 402 and spectroscopic reflectometer 404 may utilize a movable stage 410, capable moving the substrate 408 in the horizontal x-y directions as well as the vertical z direction. The stage may also rotate or tilt the substrate. In operation, the stage 410 moves the substrate 408 so that the grating structure 406 can be measured by the spectroscopic ellipsometer 402 and/or the spectroscopic reflectometer 404.

The spectroscopic ellipsometer 402 and spectroscopic reflectometer 404 also utilize one or more broadband radiation sources 412. By way of example, the light source 412 may supply electromagnetic radiation having wavelengths in the range of at least 230 to 1200 nm. Examples of broadband light sources include deuterium discharge lamps, xenon arc lamps, tungsten filament lamps, quartz halogen lamps, light emitting diodes (LEDs), and other suitable sources. Alternatively, one or more laser radiation sources may be used in combination with the broadband light source. A hot mirror 407 is placed after the source 412 in both the ellipsometer path (407a) and reflectomer path (407b) as described above. A heat management system 450 may also be utilized as previously described above.

In the spectroscopic reflectometer 404, a optical system 414 collects and directs filtered radiation from source 412 onto beam splitter 416, which reflects part of the incoming beam towards the focusing optic system 418, which focuses the radiation onto the substrate 408 in the vicinity of the grating structure 406. The optical signal produced by the substrate 408 (in this case light reflected by the substrate) is collected by the optic system 418 and passes through the beam splitter 416 to a spectrometer 420.

The spectral components are detected and signals representing such components are supplied to the processor 422 (commonly a computer), which computes the overlay in any of a number of manners known to those having ordinary skill in the art (for example, as described above).

In the spectroscopic ellipsometer 402, the light source 412 supplies light through a fiber optic cable 424 and into filter element 407a. Also the cable 424 randomizes the polarization and creates a uniform light source for illuminating the substrate 408. Upon emerging from the fiber 424, the radiation passes through an optical illuminator 426 that may include a slit aperture and a focus lens (not shown). The light emerging from the illuminator 426 is polarized by a polarizer 428 to produce a polarized sampling beam 430 illuminating the substrate 408. The radiation emerging from the sampling beam 430 reflects off of the substrate 408 and passes through an analyzer 432 to a spectrometer 434. The spectral components of the reflected radiation are detected and signals representing such components are supplied to the computer 422, which computes the overlay in any of the manners described above.

In the spectroscopic ellipsometer 402, either the polarizer 428 or the analyzer 432 or both may include a waveplate, also known as compensator or retarder (not shown). The waveplate changes the relative phase between two polarizations so as to change linearly polarized light to elliptically polarized light or vice versa.

In order to collect more information about the interaction of the incident polarized light 430 with the sample, it may be desirable to modulate the polarization state of the light or modulate the polarization sensitivity of the analyzer or both. Typically this is done by rotating an optical element within the polarizer and/or analyzer. A polarizing element within the polarizer or analyzer may be rotated, or, if at least one of those assemblies contains a waveplate, the waveplate may be rotated. The rotation may be controlled by the computer 422 in a manner known to those skilled in the art. Although the use of a rotating element may work well, it may limit the system 402. As should be appreciated, the use of rotating elements may be slow, and because there are moving parts they tend to be less reliable.

In accordance with one embodiment, therefore, the polarizer 428 is configured to include a polarization modulator 436, such as photoelastic modulator (PEM), in order to produce a fast and reliable spectroscopic ellipsometer. The polarization modulator replaces the rotating waveplate. The polarization modulator 436 is an optical element that performs the same function as a rotating waveplate, but without the costly speed and reliability problems. The polarization modulator 436 allows electrical modulation of the phase of the light without mechanically rotating any optical components. Modulation frequencies as high as 100 kHz are readily attainable.

In an alternative embodiment, the analyzer 432 is configured to include a polarization modulator such as a PEM (Photoelastic Modulator) that can be modulated electrically. In yet another embodiment, both the polarizer and analyzer contain polarization modulators, such as PEMs, that are modulated at different frequencies.

Because the polarization modulator 436 can modulate at such a high frequency, the polarization modulator 436 may be used to perform various techniques, which would otherwise be too slow. For example, the difference between the polarized reflectivity of two structures may be obtained. To do this, a PEM may be combined with an acoustic optical modulator (AOM), where the AOM rapidly moves between the two structures while modulating the polarization state at a different (but related, such as multiple or submultiple) frequency. Signals at the sum and the difference of the PEM and AOM modulation frequencies contain useful information and can be detected with high signal-to-noise by synchronous detection. Alternatively the AOM on the incident beam could be used in combination with a PEM in the analyzer.

Although not shown, the rotating waveplate may also be replaced by a polarization modulator in other types of scatterometric systems as for example a polarization sensitive reflectometer.

According to various embodiments of the invention, a hot mirror (or other wavelength extending filter that enables NIR radiation to be included in the illumination beam) may be incorporated into an illumination of an optical apparatus that may comprise any of the following or any combination of the following apparatus or metrology means: an imaging reflectometer, an imaging spectroscopic reflectometer, a polarized spectroscopic imaging reflectometer, a scanning reflectometer system, a system with two or more reflectometers capable of parallel data acquisition, a system with two or more spectroscopic reflectometers capable of parallel data acquisition, a system with two or more polarized spectroscopic reflectometers capable of parallel data acquisition, a system with two or more polarized spectroscopic reflectometers capable of serial data acquisition without moving the wafer stage or moving any optical elements or the reflectometer stage, imaging spectrometers, interferometric imaging system (e.g. Linnik microscope, e.g. Linnik microscope as implemented in the KLA-Tencor overlay measurements tools models 5100, 5200, 5300, Archer10, etc. available from KLA-Tencor of San Jose, Calif.), imaging ellipsometer, imaging spectroscopic ellipsometer, a scanning ellipsometer system, a system with two or more ellipsometers capable of parallel data acquisition, a system with two or more ellipsometers capable of serial data acquisition without moving the wafer stage or moving any optical elements or the ellipsometer stage, a Michelson interfereometer, a Mach-Zehnder interferometer, a Sagnac interferometer, a scanning angle of incidence system, a scanning azimuth angle system.

Additionally, the optical modules of any of the above described multiple optical module systems may one or more optical elements in common. For instance, a system with two or more polarized spectroscopic reflectometers capable of parallel data acquisition which share at least one optical element, with separate spectrometers or detectors for the radiation scattered from different targets. Likewise, a system with two or more spectroscopic ellipsometers capable of parallel data acquisition may have at least one optical element in common, with separate spectrometers or detectors for the radiation scattered from different targets. By way of another example, a system with two or more ellipsometers capable of parallel data acquisition may have at least one optical element in common, with separate spectrometers or detectors for the radiation scattered from different targets.

Several embodiments of an interferometer based imaging spectrometer, as well as other types of imaging spectrometers such as filter based or the "push broom" approach, are described in U.S. Patent, having U.S. Pat. No. 5,835,214, issued 10 Nov. 1998, entitled "METHOD AND APPARATUS FOR SPECTRAL ANALYSIS OF IMAGES", by Cabib et al. System and Method embodiments for film thickness mapping with spectral imaging are described in U.S. Patent, having U.S. Pat. No. 5,856,871, issued 5 Jan. 1999, entitled "FILM THICKNESS MAPPING USING INTERFEROMETRIC SPECTRAL IMAGING", by Cabib et al. An alternative architecture for spectral imaging based on LED illumination is described in U.S. Patent, having U.S. Pat. No. 6,142,629, issued 7 Nov. 2000, entitled "SPECTRAL IMAGING USING ILLUMINATION OF PRESELECTED SPECTRAL CONTENT", by Adel et al. These patents are incorporated herein by reference in their entirety for all purposes.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

The invention claimed is:

1. A method for conducting near infrared measurements of a substrate having an amorphous carbon layer formed thereon, the method comprising:

providing at least one overlay target formed as part of a substrate having a topography that includes an amorphous carbon layer formed on the substrate;

producing an illumination beam with near infrared (NIR) radiation;

filtering the illumination beam so that the filtered beam consists of a near infrared (NIR) illumination beam;

directing the NIR illumination beam onto a portion of the surface such that some of the NIR radiation passes through the amorphous carbon layer to impinge on material under the amorphous carbon layer to generate an output signal that includes NIR radiation, where the output signal that includes NIR radiation passes from the material under the amorphous carbon layer back through the amorphous carbon layer;

chromatically correcting the NIR radiation of the output signal;

detecting the chromatically corrected NIR radiation of the output signal, where detected chromatically corrected NIR radiation is configured to indicate at least one overlay metrology measurement of the at least one overlay target formed as part of the substrate having an amorphous carbon layer formed thereon; and processing the detected chromatically corrected output signal to obtain metrology measurements of the substrate.

2. The method of claim 1 wherein said near infrared measurements are used to conduct overlay metrology of an overlay target formed on the substrate, wherein, providing a substrate includes providing a substrate having an overlay target formed thereon wherein at least a portion of the target is overlaid with the amorphous carbon layer;

directing the filtered beam onto a portion of the surface includes directing the filtered beam onto the overlay target to generate an output signal comprising an overlay signal;

detecting the output signal comprises detecting the overlay signal; and processing the detected chromatically corrected output signal comprises processing the detected overlay signal to calculate overlay measurements for the overlay target.

3. A method as recited in claim 2 wherein detecting the overlay signal comprises collecting an image of the overlay signal in an NIR range.

4. A method as recited in claim 2 wherein the NIR illumination beam is limited to a near infrared range having a bandwidth of 0.75 µm (micrometers) to 1.1 µm.

5. A method as recited in claim 3 wherein detecting the overlay signal comprises collecting an image of the overlay signal in the NIR range with a CCD detector device.

6. A method as recited in claim 4 wherein the NIR illumination beam is limited to a near infrared range having a bandwidth of 0.80 µm (micrometers) to 1.1 µm.

7. A method as recited in claim 4 wherein the NIR illumination beam is limited to a near infrared range having a bandwidth of 0.85 µm (micrometers) to 1.1 µm.

8. A near infrared overlay metrology system comprising:

a movable stage that holds a substrate with an overlay target formed as part of the substrate, at least a portion of the overlay target requiring imaging through an amorphous carbon layer;

an illumination source that generates an illumination beam that includes near infrared (NIR) radiation;

a filter element that filters the illumination beam so that the beam has an operational bandwidth confined to a near infrared radiation (NIR) range with a bandwidth of 0.75 µm (micrometers) to 1.1 µm;

a beam directing element arranged to direct the beam through an objective optical system that focuses the illumination beam on the overlay target of the substrate thereby imaging through said amorphous carbon layer to generate an overlay signal, where the overlay signal passes from the overlay target under the amorphous carbon layer a second time back through the amorphous carbon layer;

a chromatically corrected focusing optical system suitable for chromatic correction in the operational bandwidth of 0.75 µm to 1.1 µm; and processing electronics configured to process a detected overlay signal and calculate overlay measurements for the overlay target, where the processing electronics are configured to detect a chromatically corrected output signal including an indication of at least one overlay metrology measurement of the substrate with the overlay target formed as part of the substrate.

9. A metrology system as recited in claim 8 wherein the filter element is configured to filter the illumination beam so that the operational bandwidth of the illumination beam is limited to an NIR radiation band having a bandwidth of 0.80 µm (micrometers) to 1.1 µm.

10. A metrology system as recited in claim 8 wherein the filter element is configured to filter the illumination beam so that the operational bandwidth of the illumination beam is limited to an NIR radiation band having a bandwidth of 0.85 µm (micrometers) to 1.1 µm.

11. A metrology system as recited in claim 8 wherein an objective and focusing optical systems are chromatically corrected to an extent such that a longitudinal chromatic aberration across the operational bandwidth across the operational bandwidth is less than about 100 nanometers (nm) and a lateral chromatic aberration across the operational bandwidth is less than about 50 nm.

12. A metrology system as recited in claim 8 further comprising a detector system comprising a detector configured for capturing images.

13. A near infrared overlay metrology system comprising:

an illumination source that generates an illumination beam that includes near infrared (NIR) radiation;

a filter element that filters the illumination beam to output a NIR illumination beam having a bandwidth of 0.75 µm (micrometers) to 1.1 µm;

an optical system arranged to direct the NIR illumination beam through an amorphous carbon layer onto an overlay target formed as part of a substrate thereby generating an NIR overlay signal;

a heat management system;

a hot mirror;

a detector system arranged to receive the overlay signal and correct chromatic aberrations in the NIR overlay signal; and processing electronics configured to process the detected overlay signal and calculate overlay measurements for the overlay target, where the processing electronics are configured to detect a chromatically corrected output signal including an indication of at least one overlay metrology measurement of the substrate having the amorphous carbon layer formed thereon.

14. A near infrared overlay metrology system as recited in claim 13 wherein the detector system includes an imaging system arranged to receive the overlay signal and obtain NIR images of the overlay signal; and the processing electronics are configured for processing the NIR images and calculating overlay measurements for the overlay target.

15. A near infrared overlay metrology system as recited in claim 13 wherein the optical system arranged to direct the beam onto an overlay target to generate the overlay signal and the detector system comprise a means for obtaining metrology measurements for an overlay target having amorphous carbon layers formed thereon.

16. A near infrared overlay metrology system as recited in claim 13 wherein the hot mirror is configured to enhance the generation of near infrared (NIR) radiation in the illumination beam.

17. A near infrared overlay metrology system as recited in claim 13 wherein the overlay target formed on a substrate includes a layer of material opaque in a visible range but at least partially transmissive to radiation in an NIR range.

18. A near infrared overlay metrology system as recited in claim 17 wherein the layer of material opaque in the visible range but at least partially transmissive to radiation in the NIR range comprises amorphous carbon material.

19. A near infrared overlay metrology system as recited in claim 18 wherein the amorphous carbon layer completely covers the overlay target formed on the substrate.

20. A near infrared overlay metrology system as recited in claim 18 wherein the overlay target comprises a second grating layer formed over a first grating layer and wherein the amorphous carbon layer completely covers the first grating layer of the overlay target.

* * * * *